(12) United States Patent
Chinowsky

(10) Patent No.: US 7,352,467 B2
(45) Date of Patent: Apr. 1, 2008

(54) SURFACE PLASMON RESONANCE IMAGING SYSTEM AND METHOD

(75) Inventor: Timothy M. Chinowsky, Seattle, WA (US)

(73) Assignee: University of Washington, Seattle, WA (US)

( * ) Notice: Subject to any disclaimer, the term of this patent is extended or adjusted under 35 U.S.C. 154(b) by 152 days.

(21) Appl. No.: 10/973,928

(22) Filed: Oct. 25, 2004

(65) Prior Publication Data

US 2005/0134860 A1 Jun. 23, 2005

Related U.S. Application Data

(60) Provisional application No. 60/514,836, filed on Oct. 24, 2003.

(51) Int. Cl.
*G01N 21/55* (2006.01)
(52) U.S. Cl. .................. 356/445; 436/518; 315/82; 315/165
(58) Field of Classification Search ............... 356/445; 436/518; 315/82, 156–159
See application file for complete search history.

(56) References Cited

U.S. PATENT DOCUMENTS 6,493,097 B1* 12/2002 Ivarsson .................. 356/630
2002/0028519 A1* 3/2002 Yguerabide et al. ........ 436/518
2004/0038264 A1* 2/2004 Souza et al. ................ 435/6

* cited by examiner

*Primary Examiner*—Layla G. Lauchman
*Assistant Examiner*—Iyabo S Alli
(74) *Attorney, Agent, or Firm*—Christensen O'Connor Johnson Kindness PLLC

(57) ABSTRACT

A surface plasmon resonance imaging system (40) and method is provided. The system (40) includes a light source (42) comprising a light-emitting diode (LED) array that is positioned at the focal point of a collimating lens (44). The light source (42) and collimating lens (44) are used to illuminate the substrate surface (50) at a range of angles dependent upon which one or more LEDs are lit. The substrate surface (50) receives light from the collimated lens (44) at a selected incident angle, which can be varied by selective illumination of one or more of the LEDs in the LED array. The system (40) further includes a detector (60) that is positioned such that it is capable of detecting an image reflected from the substrate surface (50).

25 Claims, 18 Drawing Sheets

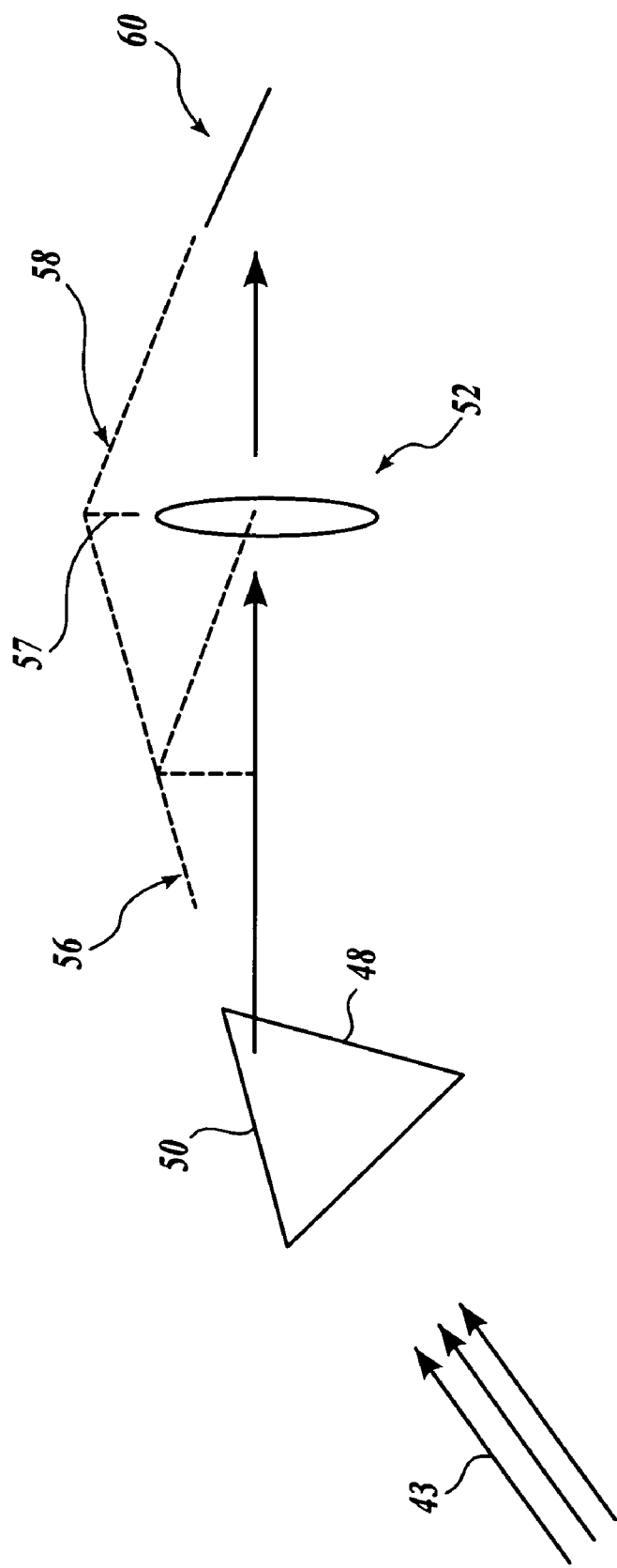

SURFACE PLASMON RESONANCE IMAGING SYSTEM AND METHOD

CROSS-REFERENCE TO RELATED APPLICATION

This application claims the benefit of U.S. Provisional Application No. 60/514,836, filed Oct. 24, 2003, which is hereby expressly incorporated by reference.

STATEMENT OF GOVERNMENT LICENSE RIGHTS

The U.S. Government has a paid-up license in this invention and the right in limited circumstances to require the patent owner to license others on reasonable terms as provided for by the terms of UO1 DE14971-02 awarded by the National Institutes of Health.

FIELD OF THE INVENTION

This invention generally relates to optical imaging and, more particularly, to an optical imaging system suitable for surface plasmon resonance imaging.

BACKGROUND OF THE INVENTION

In surface plasmon resonance (SPR) imaging, an optical imaging system is used to observe biomolecular binding events which have spatial structure. Generally, such a system includes a light source to illuminate a sample surface under conditions which produce SPR and a detector to image the light reflected from the sample surface.

FIG. 1A illustrates the SPR imaging principle. Light traveling through a high refractive index (RI) substrate 48 (e.g., BK7, n=1.51) reflects from a substrate surface, which is coated with a thin layer 51 of gold (50 nm). An aqueous sample (n=1.33), typically contained in a flowcell, contacts the opposite side of the gold. For certain wavelengths and angles of incident light, part of the incident energy will couple into a surface plasma wave traveling between the sample and the gold layer. The loss of this energy is observed as a decrease in reflectivity. Because the coupling conditions vary strongly with the refractive index of the sample, observations of reflectivity may be used as a sensitive measure of sample refractive index. Because the surface plasma wave is bound to the surface, the SPR phenomenon is only sensitive to the sample refractive index within the evanescent decay length, typically a few hundreds of nanometers. This surface sensitivity, combined with the fact that biomolecules such as proteins typically have refractive index much larger than water (n=1.6 typ.), allows the binding of biomolecules to the gold sensing surface to be detected as an increase in surface RI. To make an SPR imaging system for detection of specific substances, the gold surface is chemically functionalized (for instance by attaching antibodies to the surface) such that substances of interest will bind to the surface while other material will tend not to bind. Referring to FIG. 1A, a foundation layer 30 of biomolecules to which antibodies or other receptors (the "Y" molecules) are attached is illustrated adjacent to the gold layer 51.

FIG. 1B is a gray-scale plot that shows the tranverse magnetic (TM) reflectivity of the SPR sensing surface at various wavelengths, angles, and refractive indices. For a given refractive index (e.g., n=1.33), the plot shows the darkest region following a curve descending from approximately 600 nm at 76 degrees to 1000 nm at 64 degrees. When the refractive index increases to 1.36, for example, the dark region (the resonance position) moves higher in angle and wavelength. In SPR microscopy, both the angle and wavelength are fixed (i.e., a single x-y point is being examined on FIG. 1B), and brightness changes are observed due to changing refractive index. Thus, to sense refractive indices around 1.33, the wavelength and angle is set to some point on the dark curve for n=1.33.

Imaging the reflectivity of the sensing surface makes it possible to obtain a measurement of the refractive index at each point on the surface. The dashed curve shown in FIG. 2 illustrates the predicted variation of reflectivity with sample refractive index for monochromatic light ($\lambda$=670 nm) incident at a single angle ($\theta$=69 degrees). The solid curve shows how the response is broadened when a range of wavelengths and angles (here 30 nm and 3 degrees) are included in the illumination.

As biomolecules bind to the surface, the surface refractive index (RI) will increase roughly proportional to the quantity of the substance that has bound. Observation of the RI over time will give a "binding curve," such as those shown in FIG. 3, which reveals the quantity of bound material in real time. If the functionalization layer on the surface is patterned such that different regions of the surface tend to bind different substances, the changes in reflectivity which result as the surface is exposed to a sample may be analyzed to determine which of a number of substances are present in the sample, and in what concentration.

In optimizing an optical imaging system for use in observing SPR certain tradeoffs must be made between the following attributes, amongst others: refractive index resolution, spatial resolution and refractive index range. In particular, optimizing the detection limit of the system (in terms of molecular surface concentration) requires that the "signal" (i.e., the change in reflectivity which results from a binding event) be maximized, and that the "noise" (i.e., the uncertainty in the reflectivity measurement) be minimized, such that the signal-to-noise ratio (SNR) is maximized. With respect to spatial resolution, the optical imaging system ideally should be able to measure the variation of refractive index across the sensing surface with sufficient resolution to image any surface structure of interest. Finally, with respect to refractive index range, reflectivity increases linearly with RI for a range from approximately 1.325<n<1.335, as is shown in FIG. 2. To operate outside this range, the optical imaging system would typically be adjusted to change the incident angle and move the linear region to the desired location. Moreover, it is desirable to construct the system to require as little adjustment as possible.

In addition to optimizing the above attributes, it is desirable to produce an optical imaging system that is robust and inexpensive. Thus, it is also desirable to eliminate as many moving parts as possible and require little in the way of exotic optical components.

Therefore, there exists a need for an optical imaging system that is mechanically and optically simple, while also being capable of achieving high performance.

SUMMARY OF THE INVENTION

This invention generally relates to an optical imaging system method which is particularly suitable for surface plasmon resonance imaging. In one embodiment, the system includes a light source, at least one input optical element capable of accepting light from the light source, a substrate surface which receives light at an incident angle from the at least one input optical element, and a detector that receives light from the substrate surface and records an image. The light source is preferably a light-emitting diode array.

In accordance with another embodiment of the invention, the system further includes a resonance film disposed adjacent to the substrate surface. This resonance film is preferably a thin gold film. The resonance film creates a sensing surface that reflects the light incident upon the substrate surface.

In accordance with yet another embodiment of the invention, the at least one input optical element is a collimating lens, and the light source is positioned at the focus of the collimating lens. Preferably, the light source and the collimating lens are located in stationary positions relative to the substrate surface. Where the light source is an LED array, the angle of incidence upon which a collimated beam strikes the substrate surface can be varied by switching which one or more LEDs in the LED array are illuminated.

In accordance with still another embodiment of the invention, the system further includes at least one output optical element disposed between the substrate surface and the detector. Preferably, this at least one output optical element is a lens that is capable of accepting light from the substrate surface at a range of angles corresponding to the range of angles light is emitted from the collimating lens. The lens is preferably located in a stationary position relative to the substrate surface.

In accordance with yet still further other embodiments, the detector of the system is positioned according to the Scheimpflug angle. Particularly, the substrate surface, output optical element and the receiving surface of the detector are positioned such that the planes of each intersect in a single line. As a result, the detector's receiving surface is tilted in accordance with the tilt of the reflected image.

In accordance with yet another embodiment of the invention, an SPR imaging method for analyzing a sample disposed adjacent to a sensing surface involves providing an LED array as a light source, providing a collimating lens for collimating light received from the light source on the sensing surface, and selectively illuminating one or more of the LEDs in the array to change the incident angle of the collimated light beam on the sensing surface.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6 is a schematic diagram illustrating imaging of tilted surfaces pursuant to the Scheimpflug condition in accordance with an embodiment of the invention;

DETAILED DESCRIPTION OF THE PREFERRED EMBODIMENT

This invention generally relates to an optical imaging system particularly suitable for surface plasmon resonance (SPR) imaging that duplicates the effects of angular motion using a simplified mechanical design while also optimizing the system's attributes to enhance imaging results.

Figure 4:
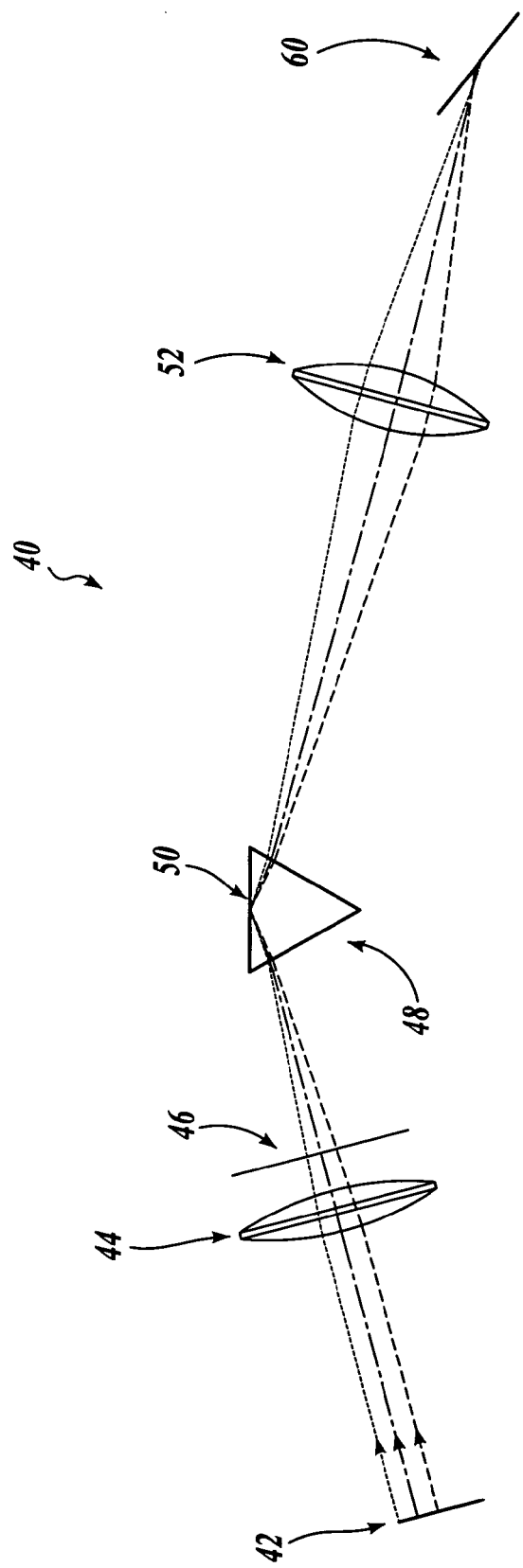
FIG. 4 is a schematic diagram illustrating an embodiment of an SPR imaging system in accordance with the invention.

FIG. 4 illustrates a schematic diagram of an SPR imaging system 40 in accordance with an embodiment of the invention. The system 40 includes a light source 42, at least one input optical element, a substrate surface 50, at least one output optical element and a detector 60. The at least one input optical element includes a collimating lens 44, which is disposed between the light source 40 and the substrate surface 50. The at least one output optical element includes a lens 52, which is disposed between the substrate surface 50 and the detector 60. The substrate surface 50 is preferably a surface of a prism 48.

In SPR imaging, light at a selected wavelength is directed through a high refractive index (RI) substrate to a sample under analysis, such as a low RI aqueous analyte, positioned adjacent to the substrate. A resonance film, preferably a gold film, is disposed between the substrate and the sample. This film interface, also referred to as a sensing surface in SPR imaging, reflects the incident light, but electrons of some of the atoms at the medium interface resonate between conduction bands. In addition, because the resonance film is extremely thin (e.g., on the order of 500 .ANG.), an electromagnetic field component of incident light penetrates a very short distance into the surface of the lower refractive index material (i.e., the sample) in the form of an exponentially attenuating evanescent wave. For incident light that is monochromatic and TM polarized, there is a specific angle of incidence at which light is absorbed rather than reflected due to resonance energy transfer between the evanescent wave and the surface plasmons. This angle, at which reflected light intensity is at a minimum, is influenced by the properties of the sample adjacent to the thin gold film.

Figure 1A:
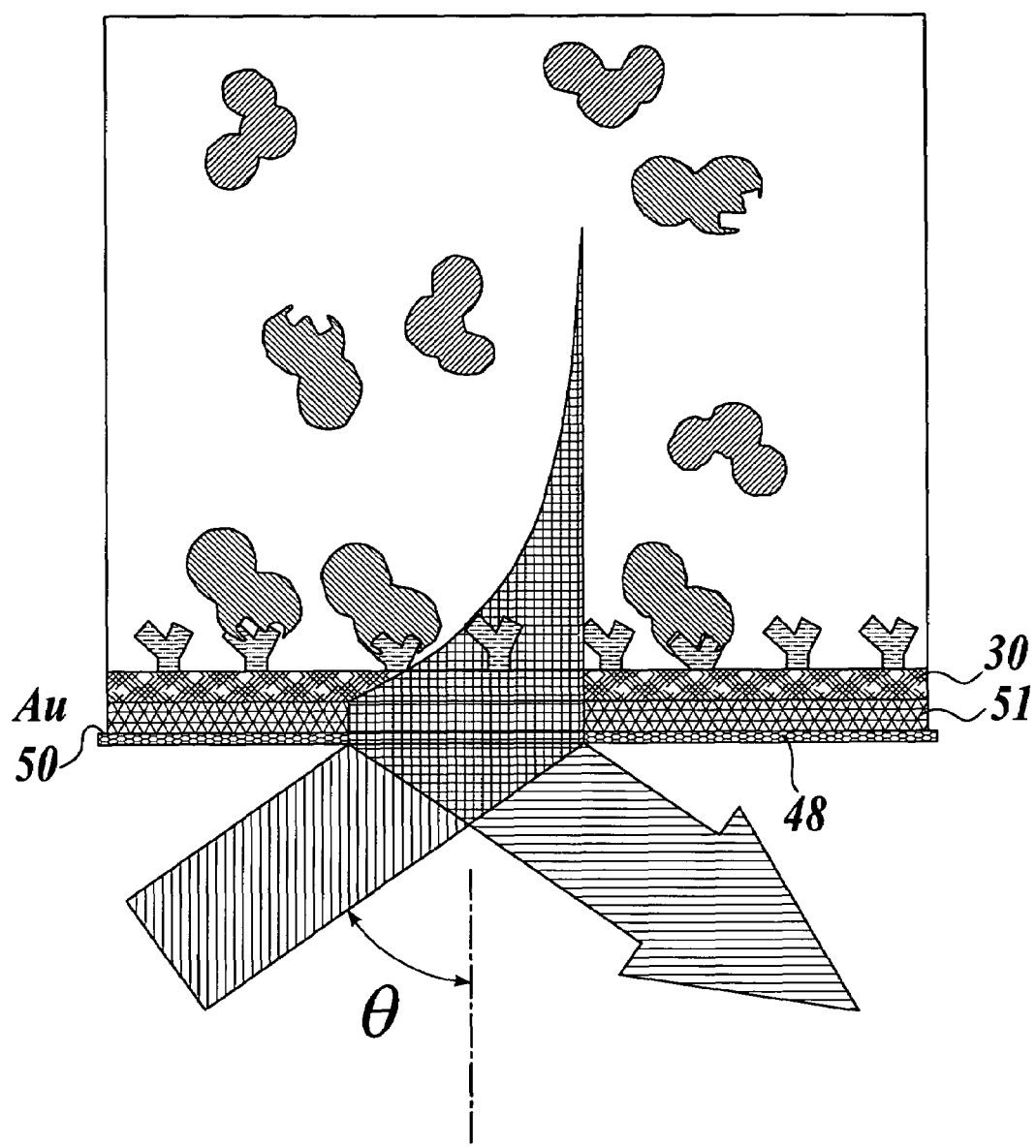
FIG. 1A is a diagram illustrating the SPR imaging principle.

While the substrate surface 50 in one embodiment of this invention could itself be coated with a resonance film 51 as shown in FIG. 1A, it is preferred that a separate substrate, such as a glass microscope slide, is coated with the resonance film, which is thereafter index-matched to the substrate surface 50 of prism 48, typically using a high-RI oil.

Returning to FIG. 4, generally, light emitted from light source 42 passes through collimating lens 44, passes through the side of the prism 48, and strikes the gold-coated sensing surface at an incident angle appropriate for observation of SPR. The reflected light passes through lens 52 and is focused onto the detector 60 which records the image.

More specifically, the collimating lens 44 accepts and collimates light received from the light source 42. The substrate surface 50 receives light from the collimating lens 44 at an incident angle appropriate for observation of SPR. As will be further described below, the light source 42 is preferably a light-emitting diode (LED) array, and the angle of incidence is varied by illuminating a selected one or more of the LEDs of the light source 42. The lens 52 is positioned such that it is capable of receiving the light reflected from the sensing surface. Moreover, the lens 52 is capable of accepting light reflected from the sensing surface at a range of angles that corresponds to the range of angles at which light is incident upon the substrate surface 50 from the collimating lens 44. The detector 60 receives light reflected from the sensing surface and focused by the lens 52 and records the image.

Even further, FIG. 4 illustrates one ray emitted from each of three different LEDs. As will be further explained below, these rays are emitted from different positions perpendicular to the optical axis and lead to different incident angles inside the prism 48. The resulting rays leaving a given point on the substrate surface 50 (which may be leaving at a range of angles) are focused by lens 52 such that they all meet again at a point on the detector plane.

Exemplary light sources for the SPR imaging system 40 include an LED, optical fiber and halogen bulb filament, amongst others, either alone as a single point source, as a line source or as an array. In any case, the light source 42 is placed at the focus of the collimating lens 42. In accordance with a further embodiment of the invention, the system 40 preferably includes one or more filters 46 for selecting the polarization and source wavelength range, for instance, if a white light source is used. If LEDs are used, which emit a narrow range of wavelengths, further wavelength filtering may not be necessary. The filter 46 is disposed between the collimating lens 42 and substrate surface 50 or anywhere else in the optical path compatible with filter properties (such as size and ability to accept light at non-normal incidence). As will be appreciated by those skilled in the art and others, the physical size and wavelength distribution of the light source 42 is adjusted such that the detector 60 operates just below saturation, and as will be explained further below, such that the greatest signal-to-noise ratio (SNR) is achieved.

To achieve a useful refractive index range, an SPR imaging system using a fixed illumination wavelength requires the ability to adjust the incident angle of illumination light. A typical imaging system physically rotates the light source and collimating optics using rotary positioners. However, this invention provides a mechanically simpler alternative. In particular, FIG. 10 illustrates that moving the light source off-axis (i.e., off the optical axis of the collimating lens 44) varies the output beam angle. This effect is true both for in-plane and out-of-plane movement. However, because the incident beam strikes the sensing surface at an oblique angle (e.g., greater than 60 degrees) the effect of out-of-plane movement on the incident angle is small. This is the point of FIGS. 9E and 9F referred to below. Essentially, moving the light source changes the angular direction of a collimated beam, and thus creates the same effect as rotating the entire collimating assembly relative to the substrate surface.

As a result, a SPR imaging system, in accordance with an embodiment of the invention, adjusts the incident angle of illumination with little or no mechanical motion, and namely by translating the light source. This replaces the need to rotate the entire collimation assembly with the need for small translations of the light source. Mechanical motion may be eliminated entirely if, rather than moving the light source, multiple light sources positioned at various locations perpendicular to the optical axis and in the plane of incidence (i.e., the plane of FIG. 4) are used. Then, as will be explained further below, when a particular incident angle is desired, only the light source at the correct position is illuminated.

Thus, in view of the above and in accordance with an embodiment of the invention, the optical imaging system includes a single light source translated across the optical axis by a manual or motorized positioner. In accordance with another embodiment of the invention, the optical imaging system alternatively includes multiple light sources such as LEDs, optical fibers, or halogen bulbs that are located at various positions across the optical axis and independently illuminated to select a collimation angle.

Figure 5A:
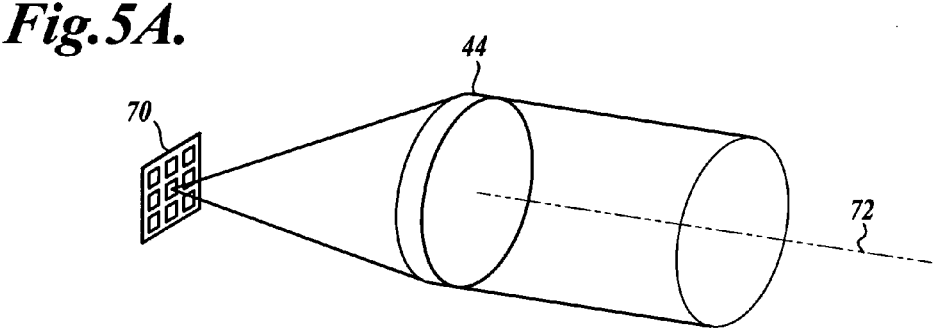
FIG. 5A illustrates the collimation of a light beam where a single LED is lit in accordance with an embodiment of the invention.

In the preferred embodiment of the invention, both the light source 42 and collimating lens 44 are stationary, and the light source is an LED array. As shown in FIG. 5A, an LED array 70 is located at the focus of the collimating lens 44. Each LED serves as point source of near monochromatic light. If a single LED is lit as shown in FIG. 5A, the collimating lens 44 will emit a nearly collimated beam of light.

Figure 5B:
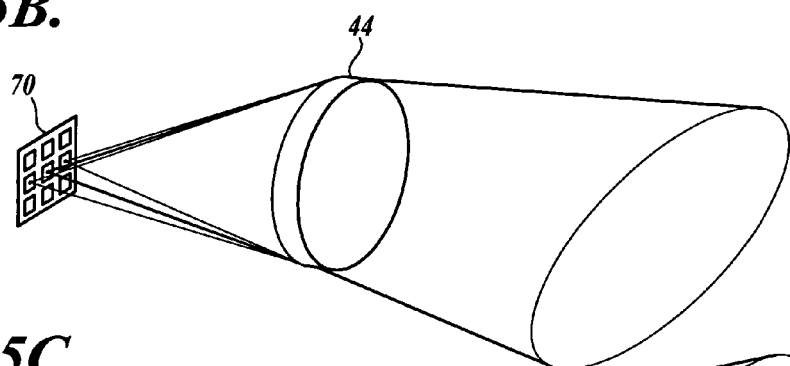
FIG. 5B illustrates the effect of a collimating lens where an entire row of LEDs is illuminated in accordance with an embodiment of the invention.

Light incident upon substrate surface 50 will have angular spread both in-plane (i.e., the plane of FIG. 4 or the plane of the system) and out-of-plane (i.e., perpendicular to the plane of FIG. 4). Both types of spread will affect the three-dimensional angle at which light is incident upon the substrate surface 50. However, in-plane angular dispersion has a much greater effect on the incident angle, i.e., the angle as measured with respect to the substrate surface normal. Out-of-plane angular dispersion will have a much smaller effect. For this reason, the size of the light source may be greatly enlarged in the out-of-plane direction without appreciable degradation of incident angle spread. Thus, illuminating an entire row of LEDs, as shown in FIG. 5B, provides the benefit of increased light throughput without appreciably degrading the incident angle spread. The line-shaped light beam resulting from illuminating an entire row of LEDs as shown in FIG. 5B passes through the collimating lens 44 and results in a beam collimated in the direction perpendicular to the row and diverging parallel to the row.

Thus, in accordance with another embodiment of this invention, the light source 42 could alternatively comprise a line-shaped light source such as a rectangular fiber bundle, array of LEDs, or long halogen bulb filament. Again, the long axis of the light source 42 is oriented perpendicular to the instrument plane (i.e., perpendicular to the plane of FIG. 4).

Figure 5C:
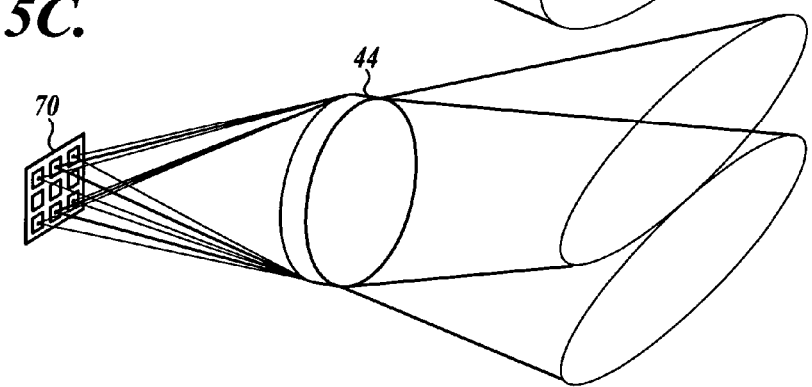
FIG. 5C illustrates the effect of a collimating lens where different rows of LEDs are illuminated in accordance with an embodiment of the invention.

As shown in FIG. 5C, depending upon which row is illuminated, the angle at which the beam emerges from the collimating lens 44 will change. By changing the angle at which the beam is capable of emerging from the collimating lens 44 by using variations of illuminated LEDs in an LED array 70, the system 40 eliminates the need for moving the light source 42 and collimating lens 44 relative to the sensing surface. Moreover, by illuminating a row in the LED array 70, light throughput is increased while also offering a range of incident angles that allows for the elimination of a moving light source.

Figure 5D:
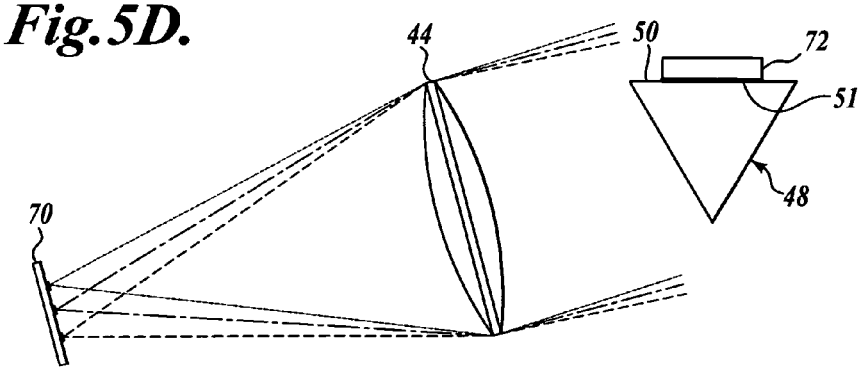
FIG. 5D illustrates the oblique illumination of a sensing surface in accordance with an embodiment of the invention.

Thus, as shown in FIG. 5D, when used for surface plasmon resonance imaging, the LED array 70 and collimating lens 44 are used to obliquely illuminate the sensing surface. FIG. 5D further illustrates a glass substrate 72 to which resonance film 51 is coated. The resonance film 51 is index-matched to the substrate surface 50 creating a sensing interface. The angle at which the beam strikes the substrate surface 50, and thus the sensing surface, changes by selecting which row or group of LEDs is illuminated. FIG. 5D illustrates each of three rows of LED array 70 illuminated. Illuminating an entire row of LEDs rather than a single LED allows great increase in light throughput. Because the incident angle is often large (e.g., 70°) the variation in incident angle due to the use of line source rather than a point source is small.

The semi-collimated light produced using the methods described above illuminates the SPR sensing surface. Any spatial variation in surface RI across this surface will cause the reflected intensity to have spatial structure. The task of the optical imaging system's output imaging optics, such as lens 52, is to form a high quality image of this structure on an image detector. If the angle of incidence is changed to accommodate a different analyte RI, the angle of the reflected light will also change, and the output imaging optics must be able to accommodate this. Similarly, if the illumination light emerges as a broad range of angles, for instance because a line source has been used to increase throughput, the output imaging optics must be able to intercept and focus all of this light, preferably without the need to move the output imaging optics.

As shown in FIG. 4, the nature of the output imaging optics is to accept rays emitted from an object point at a range of angles and focus them down onto a single image point. The range of angles and the quality of focus obtained is dependent upon implementation details, but sufficiently optimized optics will have a field of view adequate to intercept a range of angles large enough to permit adjustment-free operation over a useful range of incident angles. Thus, in an embodiment of this invention, the optical imaging system uses output imaging optics capable of accepting input light at a range of angles comparable to the range of angles emitted from the collimator. An example of such output imaging optics is a wide-field lens capable of forming a sharp image, such as a Computar TEC-55 lens.

One function of the SPR imaging system 40 is to form an image of the sensing surface on the imaging detector 60. Because the substrate surface 50, and hence sensing surface, is tilted relative to the illumination light, the image will also be tilted by an amount given by a relation termed the Scheimpflug condition. If this condition is met, the image will be in focus across the entire image plane. In the past, prior SPR imaging systems have ignored this condition and thus have tolerated the reduced depth of field that results. One reason which experimenters may not have exploited this technique in the past is the need for custom mounting of the imaging detector. Off-the-shelf cameras typically do not allow positioning of the detector at such an oblique angle. Thus, in accordance with another embodiment of the invention and as will be further described below, the SPR imaging system 40 includes a detector 60 that is mounted at the Scheimpflug angle. In particular, the detector 60 and lens 52 are positioned such that the respective planes 56, 57 and 58 of the substrate surface 50, lens 52 and detector 60 intersect at a single line. This orientation is illustrated in FIG. 6.

SPR imaging is a versatile technique for detection, quantification, and visualization of biomolecular binding events which have spatial structure, and thus has particular applicability to medical diagnostics and life sciences research and development. While this invention is generally directed to a new high-performance SPR imaging system, it will be appreciated by those skilled in the art and others that the optical imaging system disclosed herein could be useful for many applications. Other angle-dependent optical sensing techniques such as ellipsometry and Brewster angle microscopy will likewise benefit, as will imaging or illumination systems in which facile adjustment of illumination conditions is needed.

As mentioned briefly above, in order to optimize refractive index resolution, the SNR must be maximized. The "signal" in SPR imaging is the change in measured intensity caused by a change in surface RI, and may be expressed as $$S = \frac{d(I \times R)}{dn} \Delta n = I \times \frac{dR}{dn} \times \Delta n \tag{1}$$

where I is the illumination intensity, $\Delta n$ is the change in RI, and dR/dn is the derivative of reflectivity with respect to surface RI. Noise in relatively bright imaging systems is typically dominated by shot noise, i.e., statistical fluctuations in the number of photons striking each detector pixel during the detector's integration period. The magnitude of the shot noise present in a measurement (quantified by the expected standard deviation of the measurement) is given by[5]

$$N = \sqrt{I \times R} \tag{2}$$

where I is in units of photoelectrons. The SNR is then $$\frac{S}{N} = \frac{I \times dR/dn \times \Delta n}{\sqrt{I \times R}} = \sqrt{I} \times \frac{dR}{dn} \times \frac{\Delta n}{\sqrt{R}} \tag{3}$$

SNR is understandably proportional to $\Delta n$, and R will change only slightly during measurement of a typical binding event, so for measurement of a given $\Delta n$, this equation can be expressed as $$\frac{S}{N} \propto \sqrt{I} \times \frac{dR}{dn} \tag{4}$$

Figure 1B:
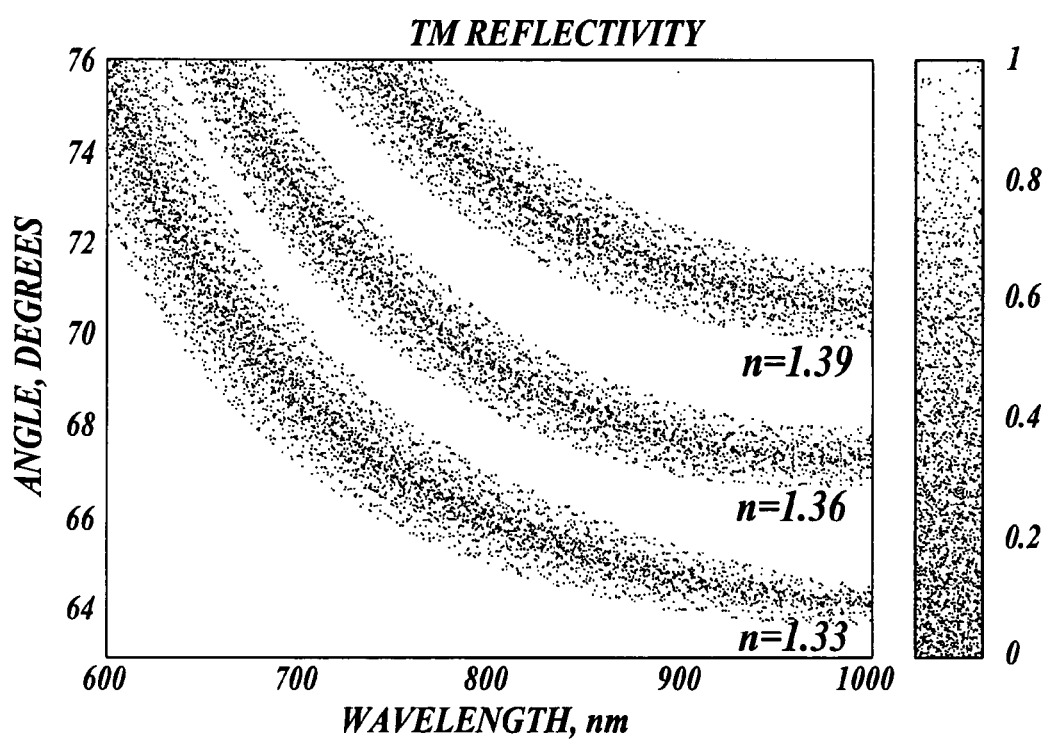
FIG. 1B is a gray-scale plot illustrating reflectivity as dependent upon the wavelength, angle of incidence, and the refractive index of the analyte close to the sensing surface.
Figure 2:
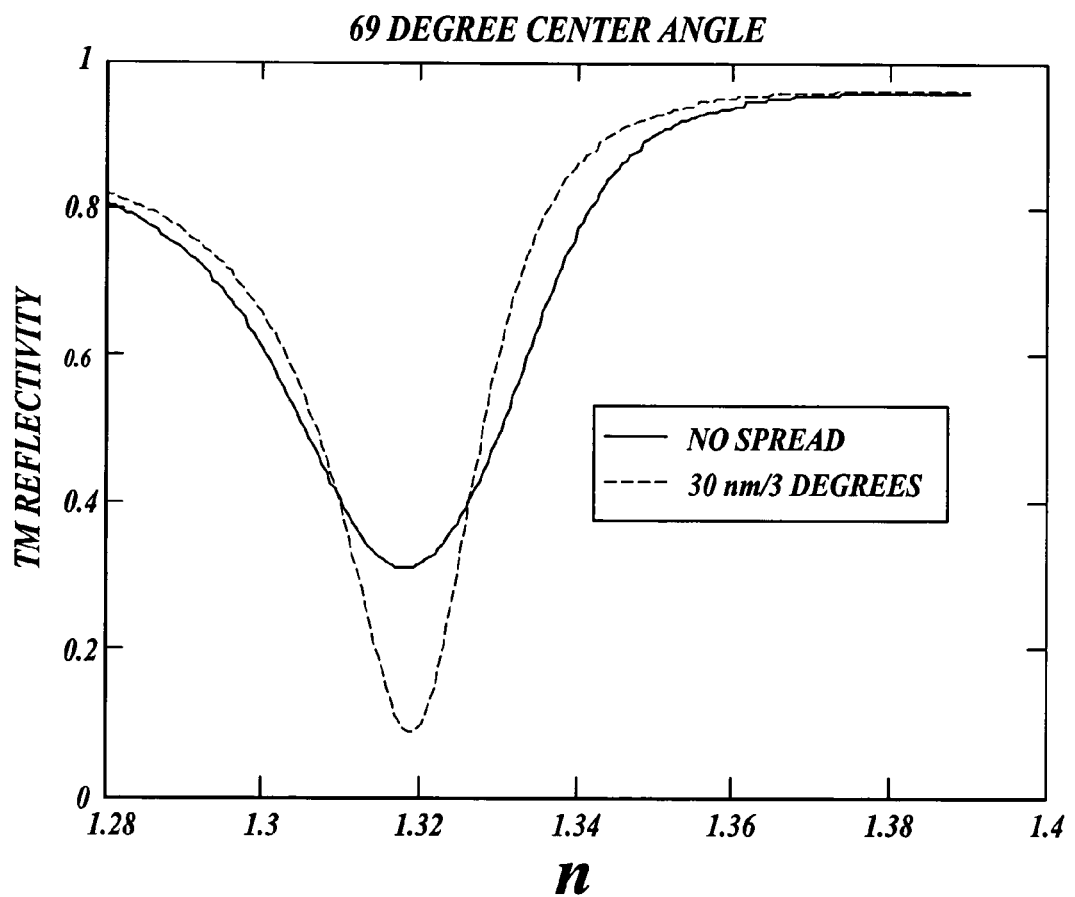
FIG. 2 is a diagram illustrating the predicted variation of surface reflectivity with refractive index.
Figure 3:
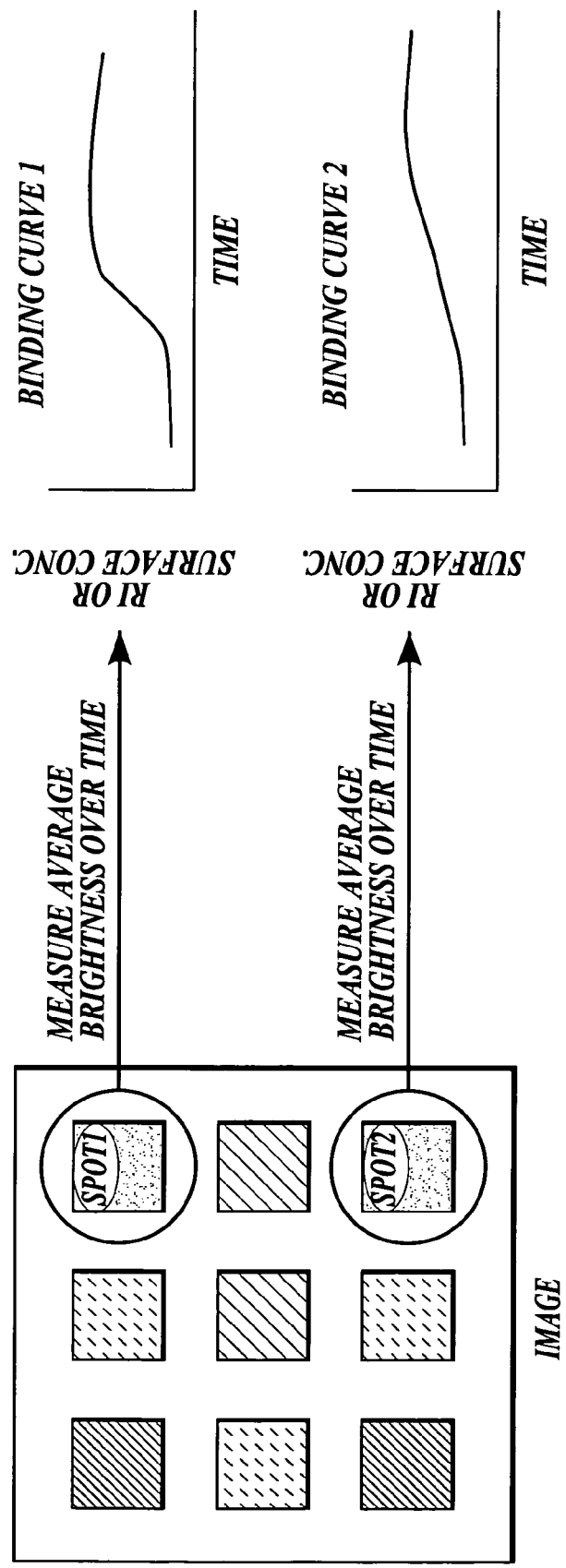
FIG. 3 is a diagram illustrating the interpretation of SPR imaging data as binding curves.

This makes plain the two options available for improving SNR: increasing dR/dn and increasing I. The main parameters available to the user for maximizing dR/dn are the illumination angle and the illumination wavelength. As shown in FIG. 1, the SPR "dip" is sharper at longer wavelengths (near infrared), resulting in greater dR/dn at those wavelengths. Choice of angle is a little more involved, because the incident angle which maximizes dR/dn varies depending upon the sample RI, but for a given illumination wavelength, such an angle can be found. For example, it can be estimated from FIG. 2 that 69 degrees is the optimal incident angle for 670 nm illumination and n=1.33. The optimal angle is where the slope of the graph is highest, which is around 1.33. Increases in I, the light source intensity, must be accompanied by changes in the detector 60 which enable an increased number of photoelectrons to be accumulated without saturating the detector 60. There are two ways in which this can be accomplished:

1. Increase pixel size. A detector which has 12 micron pixels can in general integrate 4 times the number of photons than a detector with 6 micron pixels before saturating.
2. Increase image acquisition rate. Decreased integration time with a corresponding increase in frame rate will allow a higher illumination level. Frames may be then summed after acquisition.

Large area detectors with a rapid frame rate allow the best detection statistics. A readily available detector exemplifying this principle is the Pixelink PL-A661 (½" detector, 12.7 frames/sec). A more advanced detector with greater performance is the FastVision FastCamera 13 (⅔" detector, 500 frames/sec).

As described above, an increase in light source intensity is desirable to decrease the influence of shot noise. To achieve this, a strategy for increasing intensity is needed. The absolute brightness of a light source 42 (LED, halogen bulb, laser, etc.) is limited by available technology, power requirements, and thermal management. Once the maximum practical brightness is achieved, a different strategy for increasing light throughput is required. One possibility is to increase light throughput by increasing the angle or wavelength dispersion of the illumination light.

In a real instrument, illumination light will be neither perfectly monochromatic nor perfectly collimated, but rather will contain a range of wavelengths ($\Delta\lambda$) and angles ($\Delta\theta$). The effect of this on the measurement will be that the measured reflectivity will be an average reflecting the influence of various wavelengths and angles; the corresponding dR/dn curve will likewise be given by the average of dR/dn curves for the various wavelengths and angles, weighted by the appropriate distribution. The effect of this averaging will be to make the features of the reflectivity curve broader and shallower, and therefore reduce the magnitude of dR/dn. Because SNR is proportional to dR/dn, it is therefore desirable to make $\Delta\theta$ and $\Delta\lambda$ as small as possible, all else being equal. However, in general, all else is not equal. SNR is also proportional to $\sqrt{I}$, and I may depend strongly upon $\Delta\theta$ and $\Delta\lambda$. The effects of $\Delta\theta$ and $\Delta\lambda$ on both dR/dn and I must be considered when choosing optimal values for $\Delta\theta$ and $\Delta\lambda$.

As set forth above, FIG. 4 illustrates the main components of an SPR imaging system 40 in accordance with an embodiment of the invention. Light emitted from one or more light sources passes through collimating optics and one or more filters, passes through the side of a prism, and strikes the gold-coated sensing surface at angles appropriate for observation of SPR. The reflected light passes through output imaging optics and is focused onto a detector which records the image.

A collimated light source is formed by placing a "point source" at the focus of a convex collimating lens. Rays emerging from the lens will travel in parallel. In an actual light source, the size of the "point source" will be defined by the size of a light emitting region such as a light bulb filament, optical fiber, LED die, or pinhole. The output light will have an angular spread DO related to the size of the source $\Delta d$ by $$\Delta\theta = \tan^{-1}\left(\frac{\Delta d}{f}\right) \tag{5}$$

where $f$ is the focal length of the collimating lens. The wavelength distribution of the light source will be determined by the nature of the source and by any subsequent filtering. Filtered "white light" sources, such as tungsten halogen bulbs, contain significant energy across the visible spectrum and into the infrared. To select a narrow band of wavelengths suitable for observing SPR, a filter with the desired bandwidth $\Delta\lambda$ and center wavelength is placed across the collimated beam.

Figure 7A:
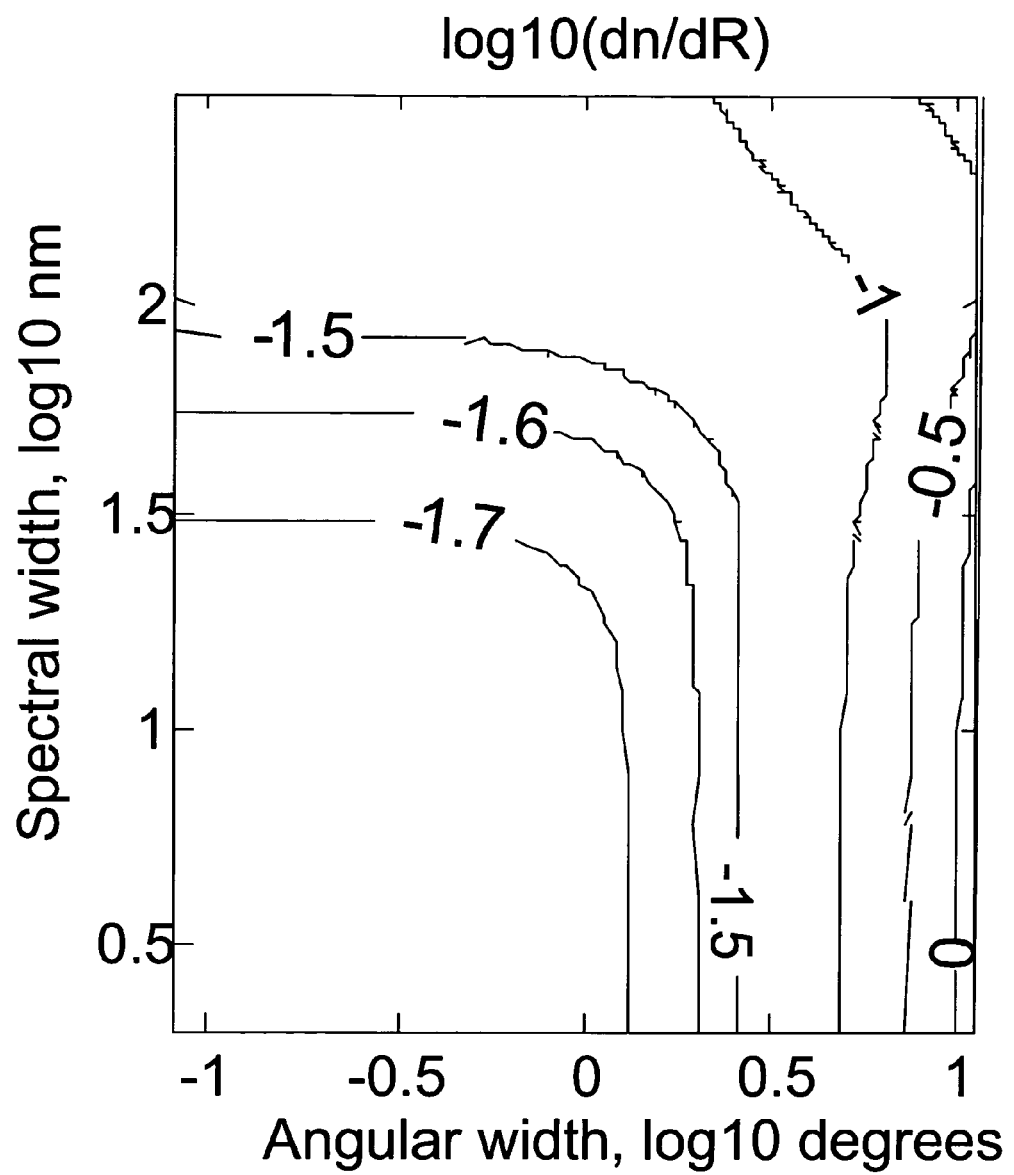
FIGS. 7A-7C illustrate the predicted dependence of SNR on light source properties.
Figure 7B:
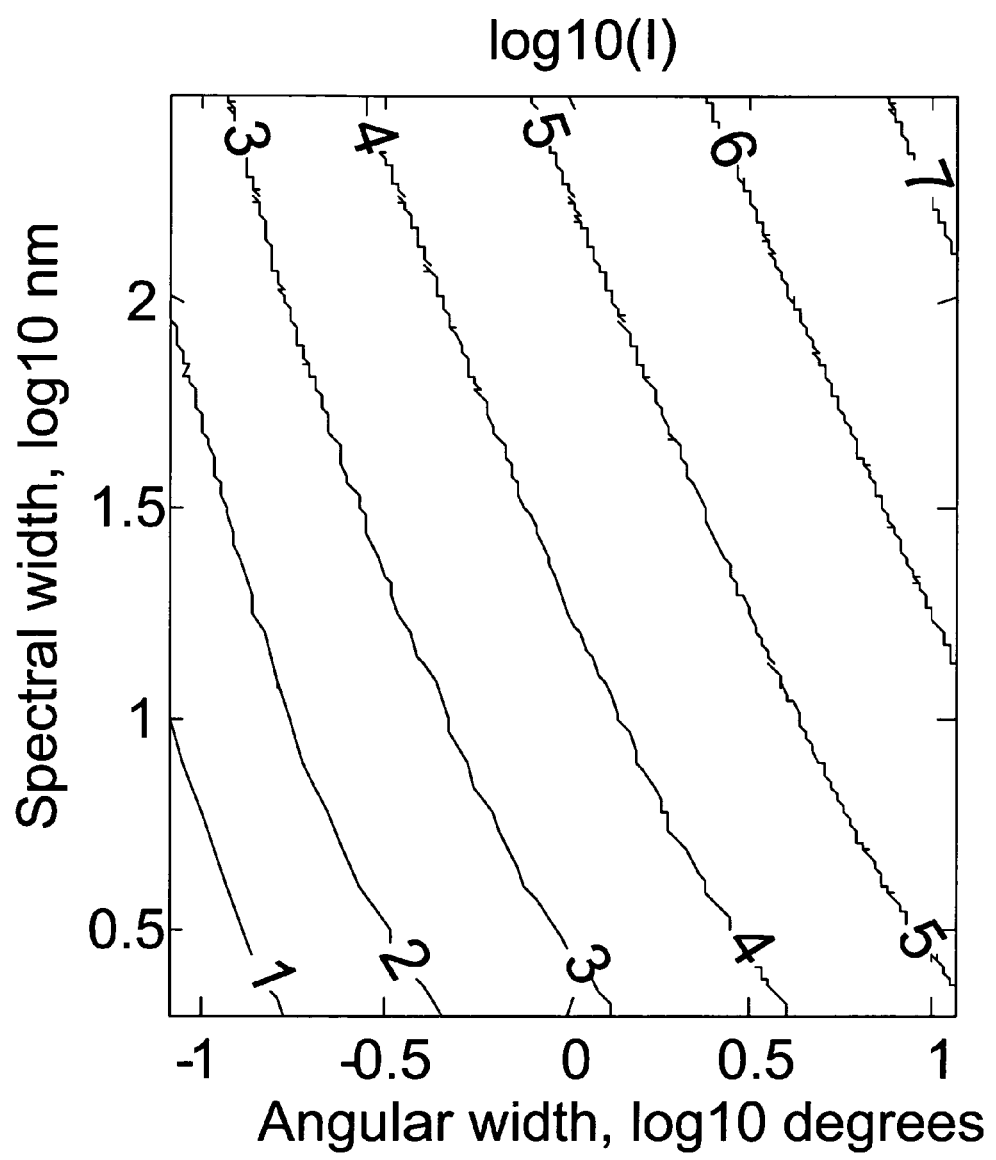
Figure 7C:
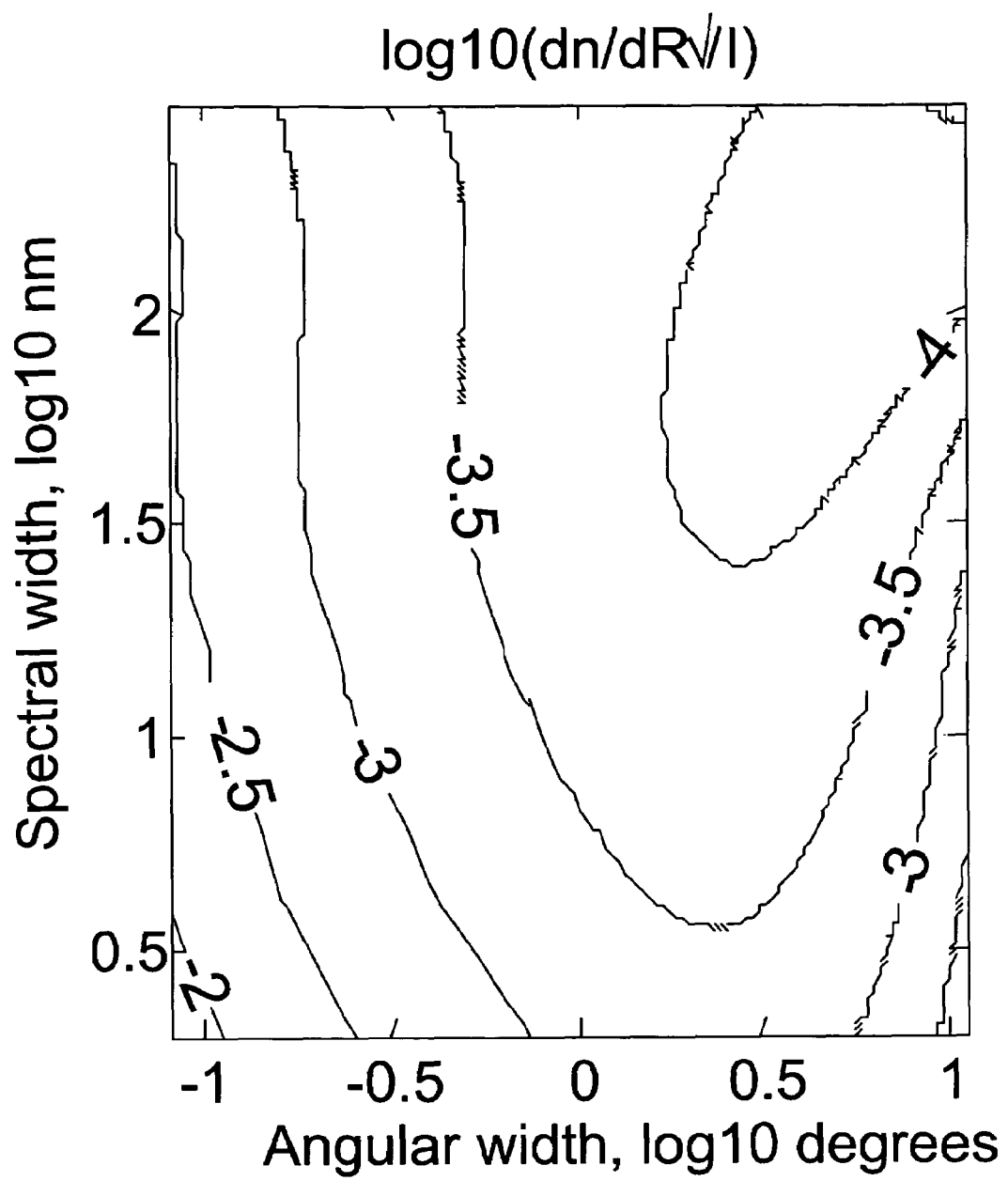

As mentioned above, the intensity I of the light exiting the collimator will typically vary with $\Delta\theta$ and $\Delta\lambda$. For the case of a white light source assumed for simplicity to have equal intensity at all wavelengths, $$I \propto \Delta\lambda \tag{6}$$

because increasing the filter bandwidth $\Delta\lambda$ allows more photons to be transmitted through the filter. If the size $\Delta d$ of the source located at the focus of the collimating optics is increased, for instance by using a larger bulb filament or optical fiber, an increase of intensity is expected and given by $$I \propto (\Delta d)^2 \tag{7}$$

because the area of the source increases as the square of its linear size. Thus, it is expected that an increase in the area of the source is accompanied by a proportional increase in intensity, i.e., that the emission per unit area is constant. Referring to equation (4), it is seen that $\Delta\theta$ and $\Delta\lambda$ have two opposing influences on the SNR—increased dispersion will reduce dR/dn, but increase I. Determination of the optimal choice of $\Delta\theta$ and $\Delta\lambda$ should take both these effects into account. This is shown in FIGS. 7A-C. These contour plots show the dependence of dn/dR (the reciprocal of dR/dn), I and (dn/dR)$\sqrt{I}$ (the reciprocal of $\sqrt{I}$ dR/dn upon the spectral width $\Delta\lambda$ and angular width $\Delta\theta$.

FIG. 7A shows that dR/dn is maximized (dn/dR minimized) when $\Delta\lambda$ and $\Delta\theta$ are small. FIG. 7B shows that increasing $\Delta\lambda$ and $\Delta\theta$ causes an immense increase in intensity—I increases by over seven orders of magnitude as $\Delta\lambda$ and $\Delta\theta$ increase. The plot of the quotient (dn/dR)$\sqrt{I}$ as illustrated in FIG. 7C shows that the beneficial effects of this increase in intensity outweigh the negative effects of increased $\Delta\lambda$ and $\Delta\theta$ on (dR/dn)—the largest SNR is now predicted for $\Delta\lambda$ on the order of 30 nm and $\Delta\theta$ on the order of 3 degrees. The dependence of R upon n for this spread is shown by the dashed trace in FIG. 2. As expected, the curve is somewhat less sharp than the curve calculated assuming no spread in wavelength or incident angle.

The improvement in SNR resulting from operation at higher intensity will only be observed if all of the additional photons can be integrated without detector saturation. This is not a trivial requirement. For example, the light throughput expected for a source with and $\Delta\lambda$=100 nm and $\Delta\theta$=10 degrees is five orders of magnitude greater than for a source with $\Delta\lambda$=100 nm and $\Delta\theta$=0.1 degree. If the light level for the latter case is sufficient to saturate the detector in ~1 second then the former case requires that detector be read out at 100,000 frames per second to avoid saturation. FIGS. 7A-C indicate, however, that increases in $\Delta\lambda$ and $\Delta\theta$ will generally improve SNR due to the benefits of increased light throughput.

As a result, given the above, an optical imaging system 40 in accordance with an embodiment of this invention includes a light source 42 such as an LED, optical fiber, or halogen bulb filament placed at the focus of a collimating lens 44, followed by one or more filters 46 to select the source wavelength range. Physical size and wavelength distribution of the source is preferably adjusted such that (1) the detector 60 operates just below saturation, and (2) the greatest signal to noise ratio, as predicted by calculations such as those shown in FIGS. 7A-C, is achieved.

To adjust the SPR imaging system for the maximum signal level for a given analyte RI, it is necessary to adjust the incident angle of illumination. As mentioned above, one method for achieving this is simply to rotate the entire light source and collimating optics as needed. However, as also set forth above, an optical imaging system 40 in accordance with an embodiment of the invention adjusts the incident angle of illumination with little or no mechanical motion, and namely by translating the light source. As shown in FIG. 4, movement of the light source perpendicular to the optical axis changes the angle of propagation of the light emerging from the collimation optics, again according to $$\Delta\theta = \tan^{-1}\left(\frac{\Delta d}{f}\right) \quad (8)$$

As described above, this replaces the need to rotate the entire collimation assembly with the need for small translations of the light source. Mechanical motion may be eliminated entirely in an SPR imaging system by replacing a single light source with an array of switchable "point sources" (such as surface mount LEDs). Switching between illumination sources then gives the user a discrete choice of illumination angles.

Figure 8A:
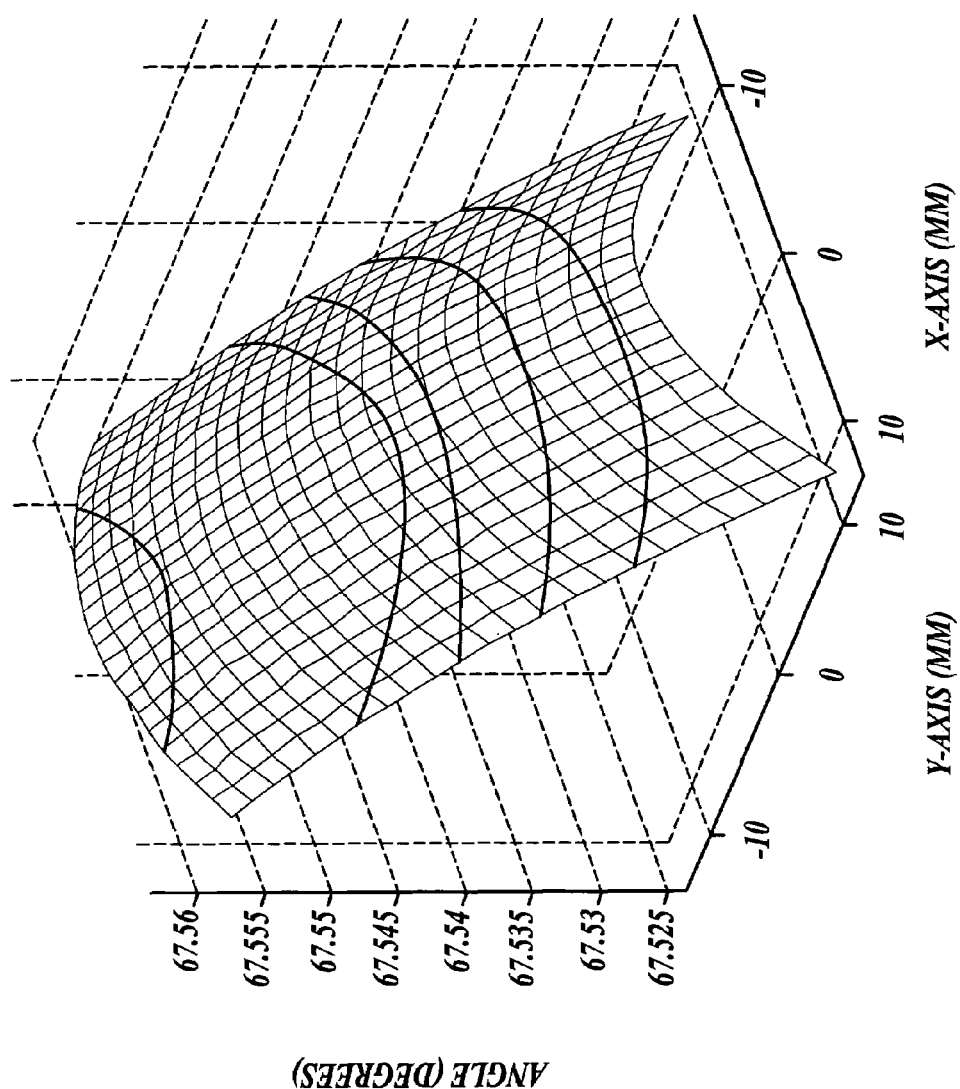
FIGS. 8A and 8B illustrate simulations of collimator performance for various light sources.
Figure 8B:
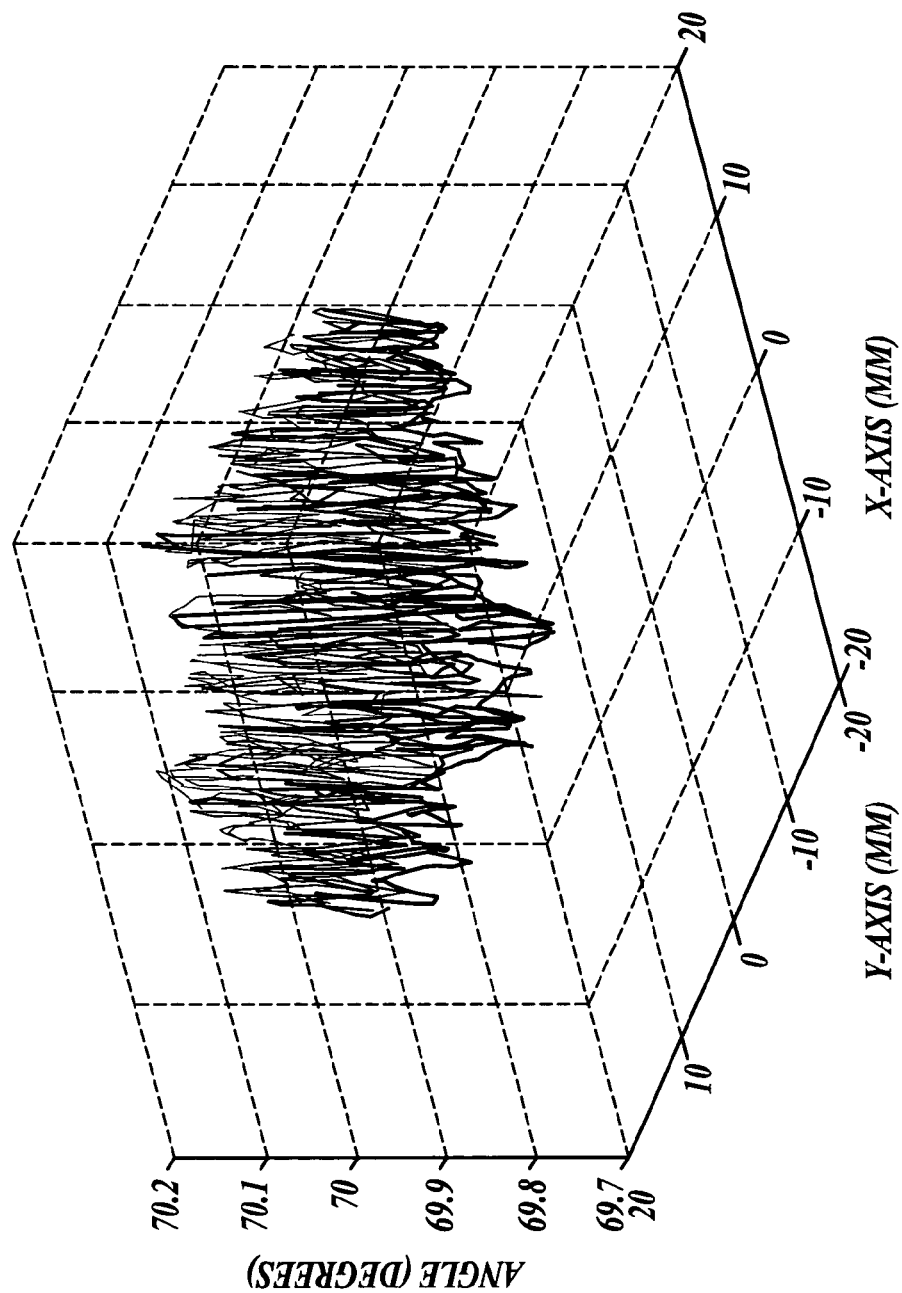

A paraxial system will yield perfect collimation if a point source is placed at the focal point of the collimating lens. FIGS. 8A, 8B, and 9A-F illustrate how the behavior of a real system compares, particularly for the case where the light source 42 has been placed off-axis to steer the output beam. FIG. 8A simulates the incident angle produced at different locations on the sensing surface for a system as illustrated in FIG. 4. In this example, a point light source 42 was assumed, and the collimating lens 44 was a 40 mm diameter, 100 mm focal length achromat. The light source 42 was placed 8 mm off-axis, changing the approximate incident angle from 70 degrees to 67.5 degrees. The results indicate that the collimation is not perfect. Rather, the incident angle varies by about 0.05 degrees depending upon location. This variation is small compared to the >1 degree spread which was shown in FIGS. 7A-C to be desirable for best SNR. To examine a configuration with greater spread, the light source 42 was changed from a point source to a 1 mm×1 mm uniform emitter (FIG. 8B). The simulation shows that every point on the sensing surface is now lit with a range of incident angles.

Figure 9A:
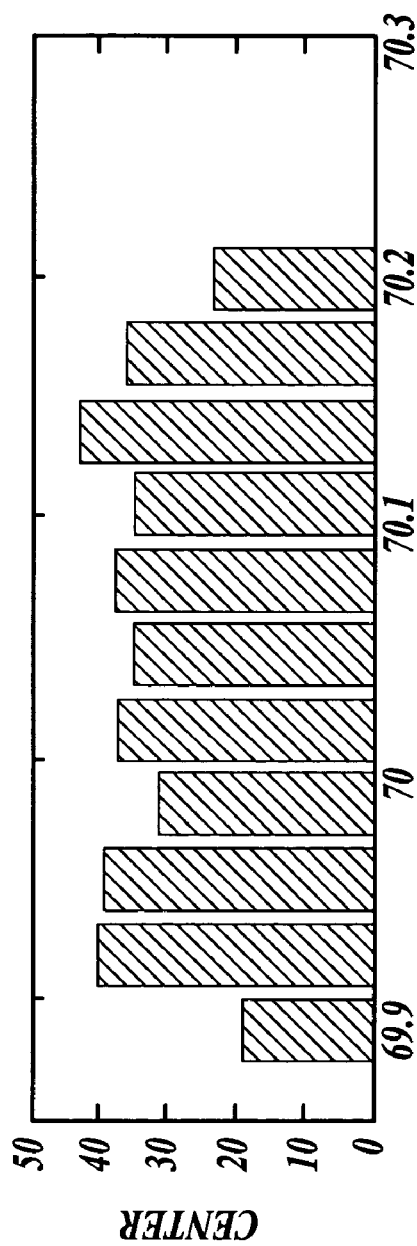
FIGS. 9A-9F are histograms illustrating predicted incident angle distribution for various light sources.
Figure 9B:
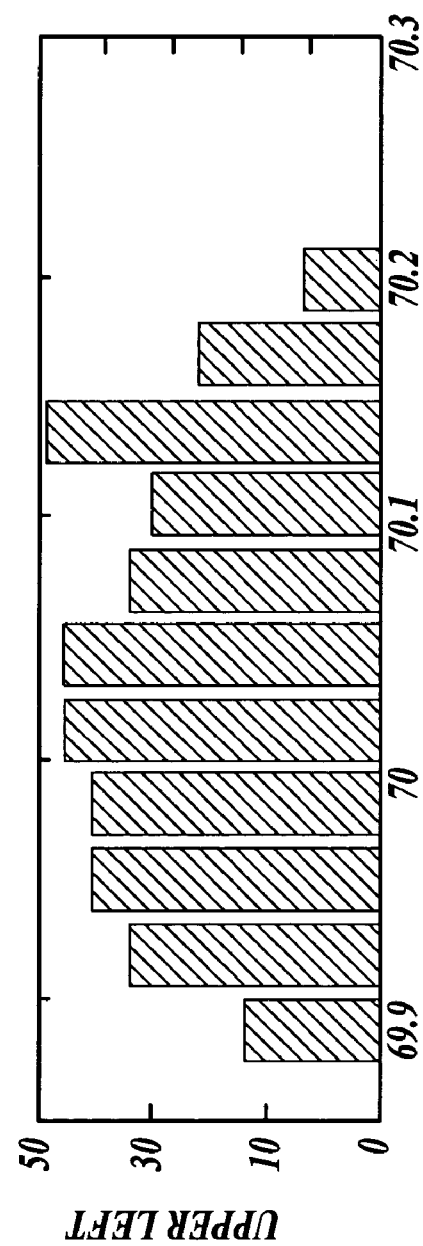
Figure 9C:
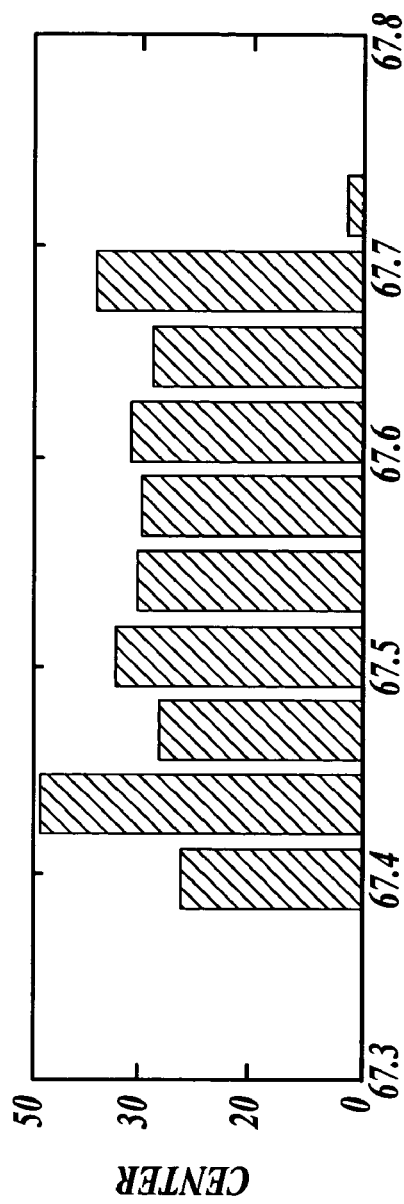
Figure 9D:
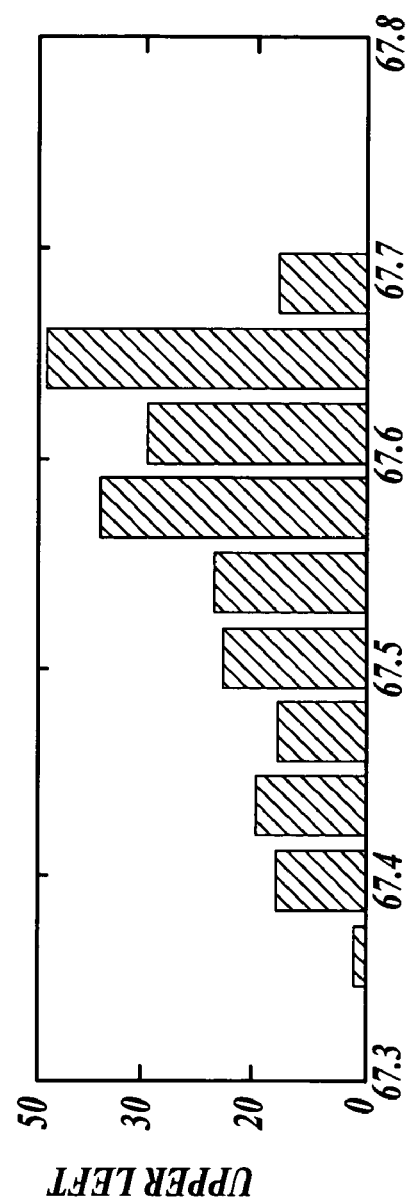
Figure 9E:
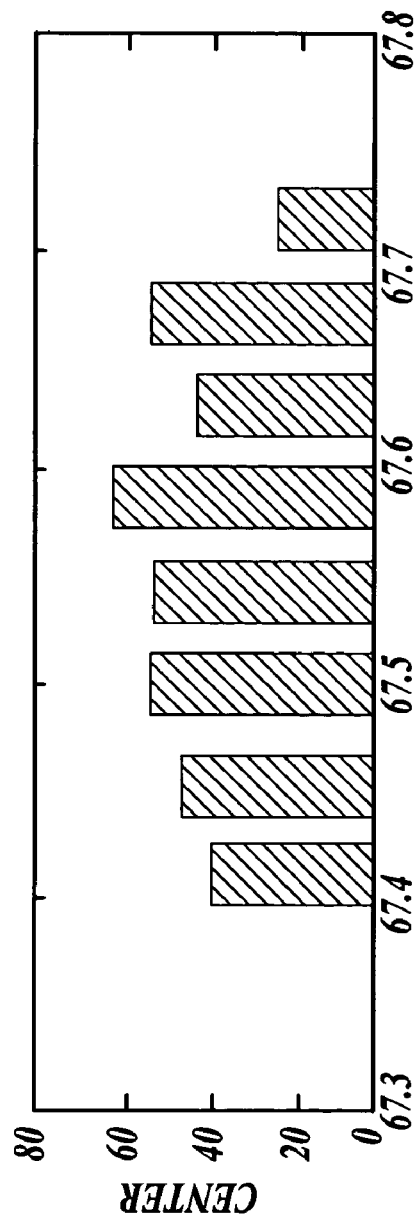
Figure 9F:
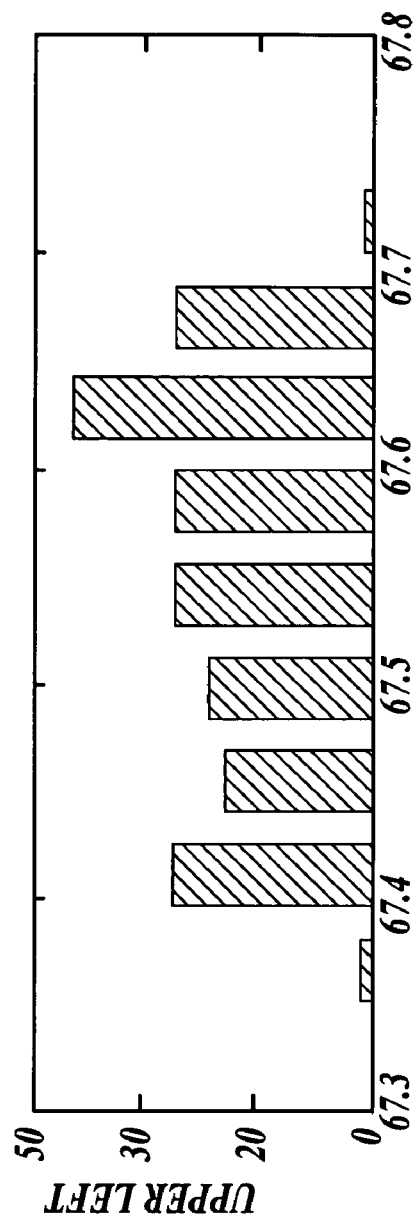
Figure 10:
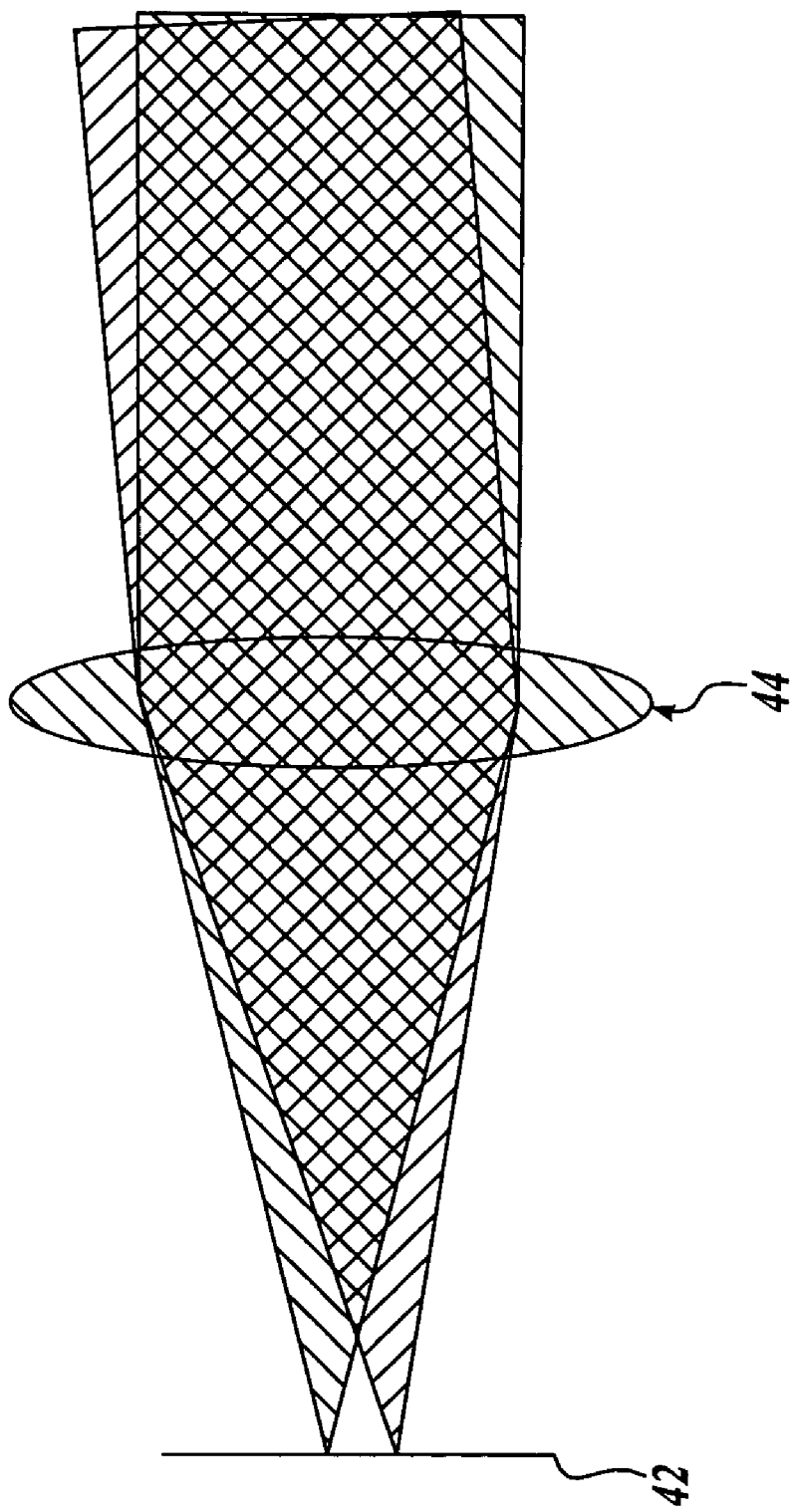
FIG. 10 is a diagram illustrating the effect of point source changes on the angular direction of a collimated beam.

For quantifying this effect, FIGS. 9A-F are histograms which show the frequency with which rays of a particular incident angle strike different regions of the detector 60. FIG. 9A-D shows the results for two 1 mm square regions, located in the center (FIGS. 9A and 9B) and upper left corners (FIGS. 9C and 9D) of the sensing surface. FIGS. 9E and 9F illustrate the results for a 1 mm×25 mm line source. As mentioned above, the line source does not appreciably increase the spread of incident angles. In fact, the distribution appears to be more uniform than that resulting from the offset 1 mm×1 mm source, which appears to have a distribution skewed to the larger angles.

As mentioned above, the method typically employed to accommodate changes in angle of incidence is to rotate the imaging optics around the sensing surface such that incident rays remain parallel to the optical axis of the imaging system. This requires rotary motion of both the imaging optics and the detector 60. To avoid rotary motion of the detector 60 and as will be explained in further detail below, the optical imaging system 40 in an embodiment of this invention relies on the intrinsic field-of-view of the optics. As shown in FIG. 4 and as explained above, the nature of imaging optics is to accept rays emitted from an object point at a range of angles and focus them down onto a single image point. The range of angles and the quality of focus obtained is dependent upon implementation details, but sufficiently optimized optics will have a field of view adequate to intercept a range of angles large enough to permit adjustment-free operation over a useful range of incident angles. Thus, the optical imaging system 40, in accordance with an embodiment of this invention, uses output imaging optics capable of accepting input light at a range of angles comparable to the range of angles emitted from the collimating lens 44.

Figure 11B:
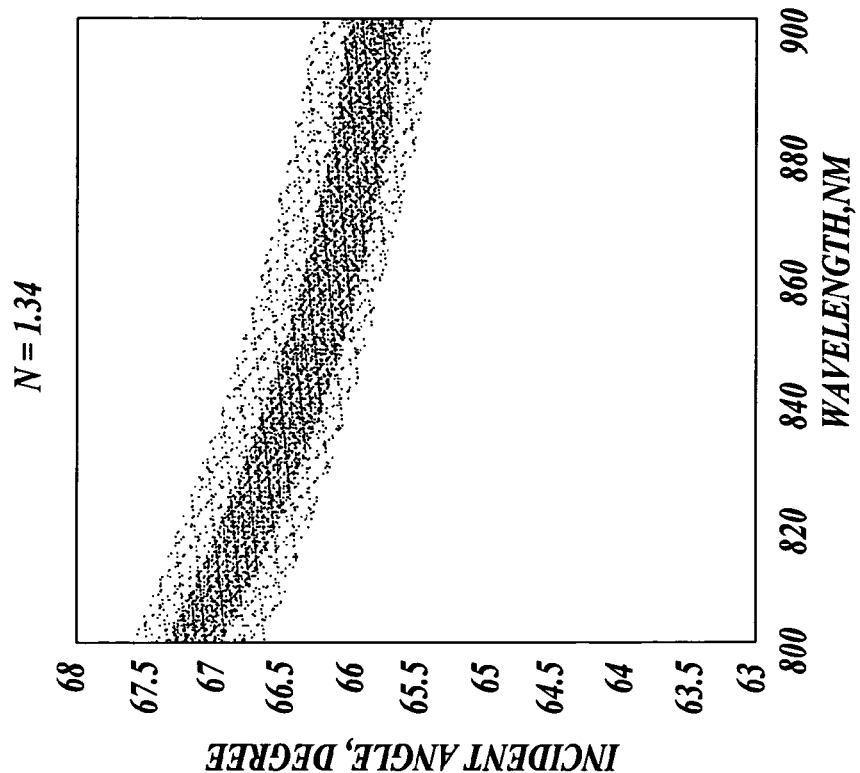
FIGS. 11A and 11B are diagrams illustrating that SPR sensing over the RI range of 1.33-1.34 requires illumination to vary only over one degree.
Figure 11A:
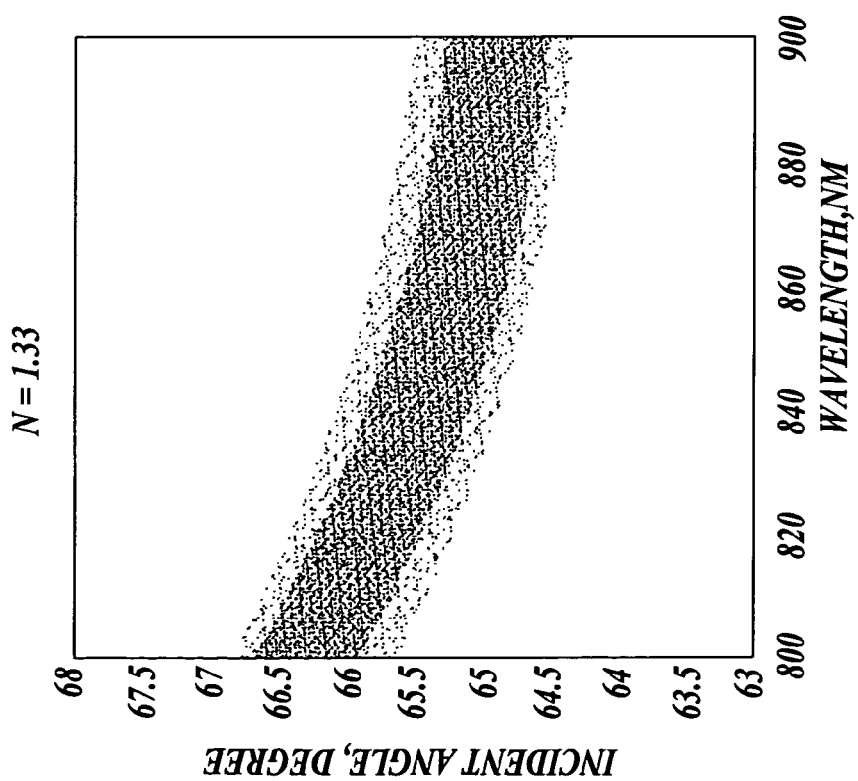
Figure 12:
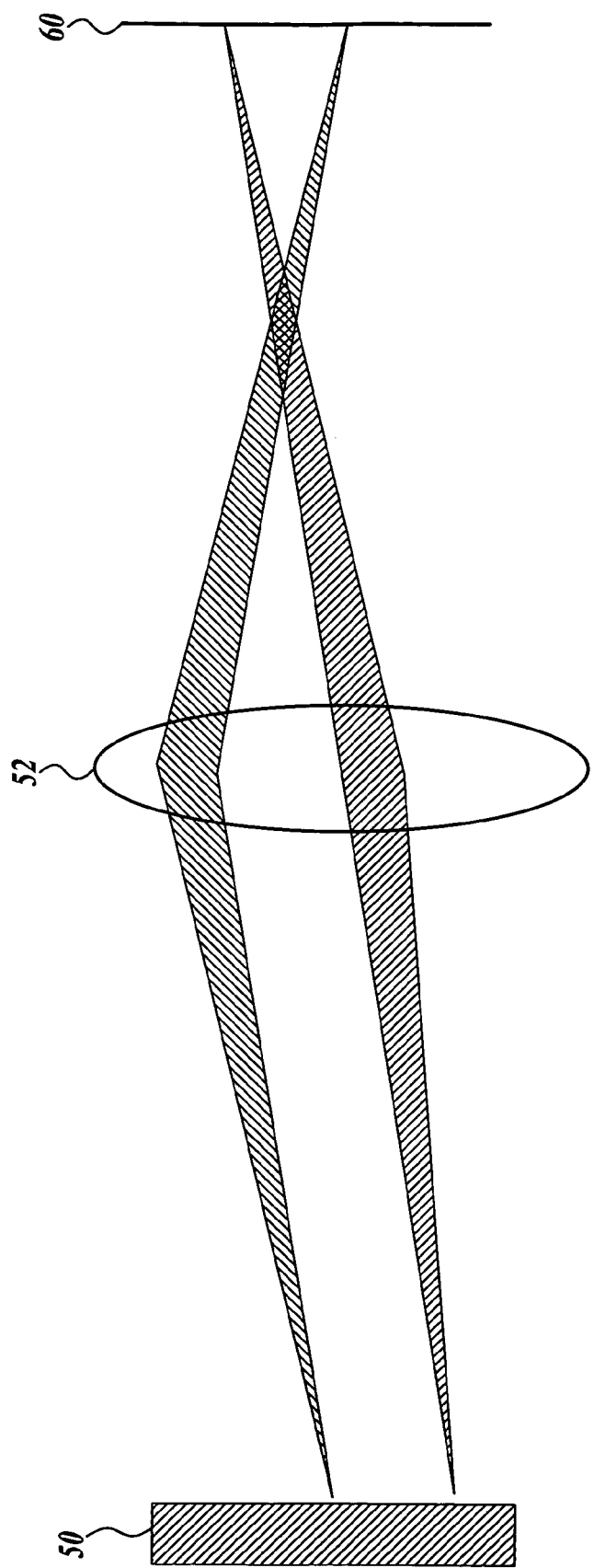
FIG. 12 is a schematic diagram illustrating the use of output imaging optics to achieve a field of view greater than one degree.

In one application, biosensing in aqueous solutions, a simulation of sensor behavior reveals a strategy for increasing the field of view. FIG. 11 illustrates the reflected intensity from the SPR sensing surface as a function of incident angle and wavelength, for two refractive indices, 1.33 and 1.34. The refractive index span of 0.01 was chosen to be greater than the maximum RI span which would typically be observed during a biosensing experiment. It is seen that the angular location of the resonance (shown by the dark bands) shifts by ~1 degree over that span. This implies that an imaging system 40 with a field of view greater than one degree will be able to image reflectivity without movement of the imaging optics. FIG. 12 is a schematic diagram illustrating the use of output imaging optics to achieve a field of view greater than one degree, without the need for mechanically rotating the output imaging optics. In this case, all input angles over the field of view are focused onto the detector 60.

Ideally the output imaging optics should be capable of intercepting and focusing all of the light reflected from the sensing surface. This light has both spatial extent (set by the size of the sensing surface) and angular extent (set mostly by the design of the illuminating optics). In addition, the quality of the focus obtained by the output imaging optics should be sufficient to resolve all features of interest on the sensing surface. The system's spatial resolution will be limited by the pixel size of the detector, and thus the spot size must be smaller than the pixel size to meet this condition. Moreover, the size of the imaging system, including the necessary working distance between the prism and the imaging lens should fit within the desired instrumentation footprint.

In SPR imaging optics, the object is tilted relative to the optical axis of the imaging optics. If a standard camera and imaging optics are used, this results in much of the object being either closer or further away than is required for best focus. The depth-of-field of the imaging optics limits the size of the object which can be imaged with high quality. SPR imaging systems in the past typically ignore this and simply accept this limited depth of field. However, the optical imaging system 40 in accordance with an embodiment of this invention uses a tilted image plane to remove depth-of-field limitations.

A tilted object will produce a tilted image. If the detector's receiving surface is tilted to match the image surface, the entire image will be in focus. The necessary detector tilt is dictated by the Scheimpflug condition, which states that if object and image are tilted such that the object plane, the image plane, and the lens plane meet in a single line, the entire image will be in sharp focus. This condition is illustrated in FIG. 6. For an SPR imaging system, the object tilt is quite large, and meeting the Scheimpflug condition may present some experimental difficulties. Lens mounts for commercially packaged imaging systems will typically block light that has a sufficiently oblique angle of incidence, and some image detectors have properties that make them unsuitable for use at oblique angles of incidence (microlens arrays, for instance). Another factor to consider is that the spot size of an out-of-focus system will decrease as the collimation is tightened, so that if a tightly collimated light source is used, the image may have adequate resolution even if it is not strictly "in focus." The use of a tilted image plane becomes more important when large depth of field is required in a system such as where the collimation of the input light has been relaxed in order to increase light throughput.

Thus, in accordance with an embodiment of the invention, the optical imaging system 40 includes a detector 60 that is mounted at the Scheimpflug angle. Moreover, the detector enclosure is preferably designed to be compatible with that oblique angle of incidence. Even further, the optical imaging system 40 preferably uses a detector 60 which is compatible with use at oblique angles of incidence.

Moreover, the number of detector pixels should be such that a sensing surface of a given size may be imaged with the desired resolution. For instance, if a 1 cm×1 cm sensing surface is to be imaged with 10 micrometer resolution, a 1000×1000 pixel detector is required assuming that the image exactly fills the detector area. Rapid acquisition and averaging of images is desirable to increase sensor SNR. There will generally be a tradeoff between the number of pixels in a detector and the maximum frame rate. Larger pixels can generally accumulate a greater number of photoelectrons before saturating. Because shot noise is expected to be the dominant noise source in SPR imaging systems, this will result in increased SNR. Uniformity and dark current are detector characteristics which are important in applications in which flat-fielding is difficult or in which light level is low. However, these characteristics are less important in SPR imaging systems, which can be readily calibrated and in which a high light level is desirable and readily produced. Based on the lack of importance of uniformity and dark current, CMOS image detectors are more desirable for the imaging system in accordance with one embodiment of this invention.

The mechanical design of the imaging system should permit easy manipulation of samples and sensing surfaces, such as would be expected of an instrument designed for use in a clinical setting. To this end, in one embodiment of this invention, the SPR imaging system is a cartridge-based system for allowing easy changing of fluidics & SPR surfaces. The system consists of a base unit, containing optics, electronics, and fluid connections. The top of the base unit contains a window through which the prism substrate surface is exposed. The window is sealed so that fluid cannot enter the inside of the base unit. A silicone manifold leads to tubing provides fluid inputs and outputs.

The SPR/fluidics cartridge preferably has a simple planar construction which is clamped to the top of the base unit. The cartridge contains a flowcell fabricated from multiple layers of laser-cut Mylar and adhesive. Holes on the bottom layer of the flowcell form fluid ports which mate to the silicone manifold in the base unit. In the center of the cartridge, a gold-coated section of microscope slide forms the bottom surface of the flow channels. To mate the cartridge to the base unit, a drop of index matching liquid is placed on the prism and the cartridge clamped on top of the base unit. The fluidic connections and the optical connection to the cartridge are made simultaneously.

The SPR imaging system described herein is useful for many applications, including those requiring (1) detection and/or quantification of biological binding events; (2) detection and/or quantification of other binding or adsorption processes; or (3) refractometry of substances or surfaces which have a spatial distribution. In addition, it will be appreciated by those skilled in the art and others that the SPR imaging system of this invention may be used for any application for which other types of SPR sensing are currently used. SPR imaging can be used, for instance, in medical diagnostics, to analyze a fluid (such as blood or saliva) and determine the concentration of a certain set of biomolecules in that fluid. To achieve this, the sensing surface would be patterned with antibodies or other receptors specific to the biomolecules of interest. When the sensing surface is exposed to a sample, target biomolecules bind to their receptors, and the SPR imaging system detects the binding event.

The optical imaging system 40 of this invention has focused on mechanical simplicity and RI resolution. In accordance with various embodiments of this invention, the use of wide-field optics and a semi-collimated light source with multiple switchable emitters allows incident angle to be adjusted without mechanical movement. Increasing light throughput by relaxing collimation and filtering requirements improves RI resolution by decreasing the effects of shot noise.

While the preferred embodiment of the invention has been illustrated and described, it will be appreciated that various changes can be made therein without departing from the spirit and scope of the invention.

The invention claimed is:

1. A surface plasmon resonance imaging system, comprising:
    a source of light at a selected wavelength, said light source comprising a light-emitting diode array;
    at least one input optical element capable of accepting light from said light source;
    a substrate surface, wherein said substrate surface receives light at an incident angle from said at least one input optical element;
    a detector for detecting an image from said substrate; and
    wherein the LEDs of said LED array are capable of being switchably illuminated.

2. The system of Claim 1, wherein said at least one input optical element comprises a collimating lens.

3. The system of Claim 1, wherein said at least one input optical element further comprises at least one filter, said at least one filter disposed between said collimating lens and said substrate surface.

4. The system of Claim 3, wherein said light source is positioned at the focus of said collimating lens.

5. The system of Claim 1, wherein said light source and said at least one input optical element are stationary relative to said substrate surface.

6. The system of Claim 1 further comprising at least one output optical element disposed between said sensing surface and said detector.

7. The system of Claim 6, wherein said at least one output optical element is a lens having a field of view greater than one degree.

8. The system of Claim 6, wherein said at least one output optical element accepts light from said substrate surface at a range of angles corresponding to the range of angles light is emitted from said collimating lens.

9. The system of Claim 8, wherein said at least one output optical element is stationary.

10. The system of Claim 1 further comprising a lens disposed between said substrate surface and said detector, said lens for focusing the image from said substrate surface onto said detector;
wherein said substrate surface, said lens and said detector are positioned such that the planes of each of said substrate surface, said lens and said detector intersect at a single line.

11. The system of Claim 1, wherein the substrate surface comprises the side of a prism.

12. The system of Claim 1 further comprising a resonance film disposed on said substrate surface.

13. The system of Claim 12, wherein said resonance film comprises gold.

14. The system of Claim 1, wherein one or more of the LEDs of said LED array is capable of being illuminated to change said incident angle.

15. The system of Claim 1, wherein said LED array is oriented such that a row of said LED array is perpendicular to the input optical axis and perpendicular to the plane of said system.

16. A surface plasmon resonance imaging system, comprising:
a source of light at a selected wavelength, said light source comprising a switchable light-emitting diode array;
a collimating lens capable of accepting light from said light source;
a sensing interface wherein said interface receives light at an incident angle from said collimating lens and wherein said collimating lens is located in a stationary position relative to said sensing interface; and
a detector for detecting an image received from said sensing interface.

17. A surface plasmon resonance imaging system, comprising:
a source of light at a selected wavelength, wherein said light source is an array of switchable point sources;
a collimating lens capable of accepting light from said light source;
a sensing interface wherein said interface receives light at an incident angle from said collimating lens and wherein said collimating lens is located in a stationary position relative to said sensing interface; and
a detector for detecting an image received from said sensing interface.

18. The system of Claim 16, wherein said light source is located in a stationary position relative to said sensing surface.

19. The system of Claim 16 further comprising an output lens stationarily disposed between said sensing interface and said detector.

20. The system of Claim 19, wherein said output lens is capable of accepting light from said sensing interface at a range of angles corresponding to the range of angles light is capable of being emitted from said collimating lens.

21. The system of Claim 19, wherein said sensing interface, said output lens and said detector are positioned such that the planes of each of said sensing interface, said output lens and surface of said detector intersect in a line.

22. A SPR imaging method for analyzing a sample disposed adjacent to a sensing surface, said method comprising:
providing a light source, said light source comprising a switchable LED array;
providing a collimating lens for collimating light received from said light source on said sensing surface; and
selectively illuminating one or more of the LEDs in said LED array to change the incident angle of the collimated light beam on said sensing surface.

23. The system of Claim 17 further comprising an output lens stationarily disposed between said sensing interface and said detector.

24. The system of Claim 23, wherein said output lens is capable of accepting light from said sensing interface at a range of angles corresponding to the range of angles light is capable of being emitted from said collimating lens.

25. The system of Claim 23, wherein said sensing interface, said output lens and said detector are positioned such that the planes of each of said sensing interface, said output lens and surface of said detector intersect in a line.

* * * * *